United States Patent
Stange

[11] Patent Number: 5,500,599
[45] Date of Patent: Mar. 19, 1996

[54] METHOD AND APPARATUS FOR THE MEASUREMENT OF THE DIELECTRIC CONSTANT OF SAMPLE MATERIALS

[75] Inventor: Gerd Stange, Nortorf, Germany

[73] Assignee: Nu-Tech GmbH, Germany

[21] Appl. No.: 348,153

[22] Filed: Nov. 28, 1994

[30] Foreign Application Priority Data

Dec. 8, 1993 [DE] Germany .................. 43 42 505.4

[51] Int. Cl.⁶ .................................................. G01R 27/26
[52] U.S. Cl. ................... 324/634; 324/632; 324/636; 324/647
[58] Field of Search ................................. 324/634, 632, 324/636, 647

[56] References Cited

U.S. PATENT DOCUMENTS

| | | | |
|---|---|---|---|
| 2,792,548 | 5/1957 | Hershberger | 324/636 |
| 3,551,806 | 12/1970 | Sasaki | 324/636 |
| 3,946,308 | 3/1976 | Miura | 324/636 |
| 4,297,874 | 11/1981 | Sasaki | 324/636 |
| 4,303,818 | 12/1981 | Smith | 324/636 |

FOREIGN PATENT DOCUMENTS

2730577  1/1978  Germany .

*Primary Examiner*—Kenneth A. Wieder
*Assistant Examiner*—Jose M. Solis
*Attorney, Agent, or Firm*—Nixon & Vanderhye

[57] ABSTRACT

An apparatus and a method for the measurement of the complex dielectric constant of a material by evaluating the amount of detuning introduced by the presence of the material. In order to simplify the circuitry required for measurement and evaluation according to the invention there are provided two rf resonators (8, 8') of the same construction, each of them comprising a dielectric solid state resonator (1, 1') in a case having a first conductive section (2, 2') and a second section (3, 3'), which is permeable for alternating fields. Both the rf resonators are positioned to each other in such a way as to provide a shielding effect by their conductive case sections (2, 2') against mutual interference and to have their sections permeable for electromagnetic fields (3, 3') facing towards the material to be measured. The operating rf frequency coupled to both the rf resonators and/or the resonance frequencies of the rf resonators (8, 8') are selected in such a way that, in the absence of the material to be measured, the common operating frequency is centered between the resonance frequencies of the rf resonators (8, 8'). On the basis of the measured amplitude values of the rf signals received in both the rf resonators and their sum and difference values the complex dielectric constant may be determined. Therefore, the need of a complete sampling of the resonance curves of the rf resonators is eliminated.

19 Claims, 4 Drawing Sheets

METHOD AND APPARATUS FOR THE MEASUREMENT OF THE DIELECTRIC CONSTANT OF SAMPLE MATERIALS

The invention relates to a method and to an apparatus for the determination of the complex dielectric constant of a sample material by analysing the amount of rf resonator detuning introduced by the presence of the sample matter, wherein the apparatus comprises an rf transmitter system transmitting rf electromagnetic fields of selected frequency into the rf resonator, an rf receiver system for the resonator field and a measuring unit connected thereto, which allows the determination of the amplitudes of the received rf signals.

A number of different methods is known for the determination of the properties of dielectric materials, wherein these dielectric properties are typically described by the relative dielectric constant $\epsilon_r$ and the loss angle $\tan(\delta)$ or as the complex dielectric constant $\epsilon = \epsilon' - i\epsilon''$. Such methods are for example used to determine the humidity of a material. These procedures make use of the large dielectric constant and the large loss angle of water contained in the sample matter and play an important role in industrial applications, e.g. in the humidity measurement of chemicals, food, tobacco, coffee, etc.. When applying microwave resonance methods for humidity measurements the sample matter under investigation will be placed inside a cavity resonator and the amount of detuning due to the presence of the matter will be measured by variation of the rf frequency and sampling of the resonance curve. From the tune shift of the resonance frequency and from the increase in resonance band width or the change of quality factor respectively of the resonator the dielectric constant of the sample matter may be deduced at known composition and density of the matter. Usually this requires calibration curves which may be obtained from previous measurement of the respective sample matter at different humidity contents. Most of the known methods furthermore require calibration measurements of the density.

From the DE—OS 40 04 119 a method for the determination of the humidity with a cavity resonator is known, which by a proper selection of the field configuration inside the sample under consideration allows the independent determination of humidity and density, where the resonance frequency and the bandwidth are determined and analysed by sampling the complete resonance curve. Here it is also necessary to place sample material inside the resonator cavity.

From the article "Ein Dielektrizitätskonstanten-Messplatz zur Untersuchung optischer Kristalle im Mikrowellenbreich" in: Kristall und Technik, Bd. 10, Nr. 6 1975, p. 695–700, by E. Wehrsdorfer et al., a similar method as the above is known, wherein the dielectric constant of a sample is determined by loading a cavity resonator operated in the microwave range of frequencies. The changes in resonance frequency and quality factor due to the presence of the sample matter are determined by measurement of the resonance curve after exposition to the sample.

For most of the industrial applications the known resonance methods for the determination of the dielectric properties of matter are disadvantageous as they require the sample under investigation to be placed inside the resonator under exactly defined conditions. In continuous manufacturing and production processes these known methods allow to take random samples only from time to time which are to be measured under relatively high efforts inside the cavity resonator. Such a random sample measurement allows access to the interesting measurement quantities with a time delay only. Furthermore it will not be guaranteed, that the material properties will not change compared to the material flow to be measured between the time the sample is taken and the following measurement. In a continuous manufacturing and production process it would be preferred to have continuous access to the momentary values of the dielectric measurement quantities and those deduced therefrom as e.g. the humidity. This however is principally impossible with methods working with cavity resonators.

From the DD-PS 138 468 a method for the measurement of the complex dielectric constant of dielectric plates is known, which are metallized on one side. For the measurement a dielectric resonator excited in its $E_{011}$-mode is placed on the non-metallized side of the plate. The metallized side acts as a termination of the resonance system. From the change of the resonance frequency compared to the case where the resonator is directly placed on a metallic plate, the dielectric constant of the plate material may be determined at a known thickness. The disadvantage of this method is that only plates with a single side metallization may be measured; furthermore the complete resonance curve has to be sampled for every measurement to determine the resonance frequency.

Experiments with "open" cavity resonators, e.g. chambers with slot-like openings, which would allow the interaction between the resonator field and some matter outside the resonator, did not lead to satisfactory results, since on the one hand they showed a relatively low sensitivity and on the other hand the amount of microwave power radiated is relatively high.

Furthermore all known sensor devices lack from the disadvantage that they require many measuring points at different frequencies radiated into the resonator in order to determine the resonance curve from this number of measuring points, from which the resonance frequency and the bandwidth finally have to be determined. This procedure causes a considerable effort in circuitry, since a large number of measured quantities at different frequencies must be obtained, stored and subsequently analysed.

It is an object of the present invention to provide a method and an apparatus for the determination of the dielectric properties of matter by analysis of the amount of detuning of an rf resonator under the presence of this matter, which allow the continuous and non-delayed determination of dielectric properties of interest.

It is a further object of the present invention to provide a method and an apparatus for the determination of the dielectric properties of matter with simpler circuitry for analysis.

It is a further object of the present invention to provide a method and an apparatus for the determination of the dielectric properties of matter for further determination of the humidity, the density of a material or the thickness of a material layer.

These and other objects are solved according to the present invention by a method comprising the steps:

using two rf resonators each comprising a dielectric resonator in a case having a first section, which surrounds the solid state resonator at least in one hemisphere with conductive material, and a second section, which is permeable for electromagnetic alternating fields, and directing said two rf resonators towards the material to be measured in such a way, that their second case sections are facing the material and that their first case sections shield against mutual interference due to electromagnetic fields emanating from the second case sections, tuning the first and the second rf resonator by a tuning means in such a way that, in the absence of the material under investigation, the first and the second resonator have a first ($\omega_{01}$) and a second ($\omega_{02}$) resonance frequency, respectively, with the second frequency being different from the first, and supplying both rf resonators with an electromagnetic field of a frequency ($\omega$), which is centered between the first ($\omega_{01}$) and the second ($\omega_{02}$) resonance frequency, and supplying the measured amplitude values of the received rf signals in said two resonators to a control and analysis means and determining the dielectric constant of the material under investigation in the control and analysis means on the basis of the sum and difference values of the measured amplitude values using predetermined relationships.

According to the present invention there are two rf resonators of identical construction for the measurement of the dielectric properties of the sample matter under investigation, which comprise a dielectric solid state resonator. It has been found that solid state resonators have properties meeting the requirements for applications in rf-measuring devices for dielectric material properties. Namely the electromagnetic field is not confined inside the resonator dielectric material but rather a nonvanishing field exists outside the resonator body. This outside field rapidly decays so that no problems arise with elelectromagnetic field energy being radiated. On the other hand due to the nonvanishing field outside the resonator sufficient sensitivity is provided for the presence of matter close to the resonator. The signals measured are those induced into a receiving means close to the solid state resonators, which may be demodulated via known measurement circuits, e.g. peak value rectification.

The solid state resonators are each located in a case which in a first section surrounding at least one hemisphere consists of condutive material and in a second section consists of material permeable for electromagnetic fields. Both of the rf resonators are positioned to each other in such a way that their conductive case sections shield the solid state resonators from mutual influences of the other resonator and that the permeable sections are directed towards the matter under investigation. A shielding of the solid state resonators against each other by conductive case sections is preferred since both the rf resonators have to be located close to each other in order to be directed to the same domain or closely neighbouring domains of the matter under investigation.

The same rf fields are coupled into both the rf resonators, i.e. both resonators will be operated at the same frequency, wherein this frequency is selected in such a way that it is exactly centered between the resonance frequency of the first resonator and the pre-adjusted different resonance frequency of the second resonator in the absence of matter to be measured. The detuning introduced by the presence of matter under investigation leads to a shift of both resonance curves and to a shift of the working points on the corresponding resonance curves at the constant operating frequency and at the same time to a broadening in bandwidth for both resonators (change of quality factor), where both these effects influence the measured amplitudes of the resonator fields. By taking the sum and the difference of the fields measured on both resonators in the presence of sample matter it is possible to completely determine the dielectric properties of this matter; this evaluation will take place in a control and analysis means, which receives the amplitudes measured, computes their sum and difference values and either applies analytical formula for their relation to the complex dielectric constant or empirical calibration curves.

It will be appreciated that the method according to the present invention completely avoids sampling of the resonance curves and that both resonators may be operated with the same constant frequency. This results in a considerable simplification of the apparatus. Further, the adjustment of the frequencies of the apparatus according to the invention is very simple when, in absence of the matter under investigation the operating frequency and the resonance frequencies of the rf resonators are adjusted in such a way, that both the rf resonators give output signals of equal amplitudes, whereby it will be guaranteed that the operating frequency is exactly centered between the resonance frequencies of the resonators, since the resonators have identical but shifted resonance curves.

According to the invention material investigations may be performed continuously and without the need of taking extra samples by placing both the rf resonators as to have a shielding effect of their conductive sections and the permeable sections directed towards the material flow, which thus may be investigated continuously and without time delay.

A further advantage of the invention is the compact and robust construction possible with dielectric resonators compared to cavity type resonators.

The invention is of special importance for the determination of the humidity content of matter, which may be deduced from the dielectric properties. In addition the method is appropriate for all those measurement and control tasks, which are based on dielectric material properties, e.g. the determination of the thickness of a layer of known material.

BRIEF DESCRIPTION OF THE DRAWINGS:

In the following the invention will be explained by way of example with reference to accompanying drawings, wherein.

Figure 1:
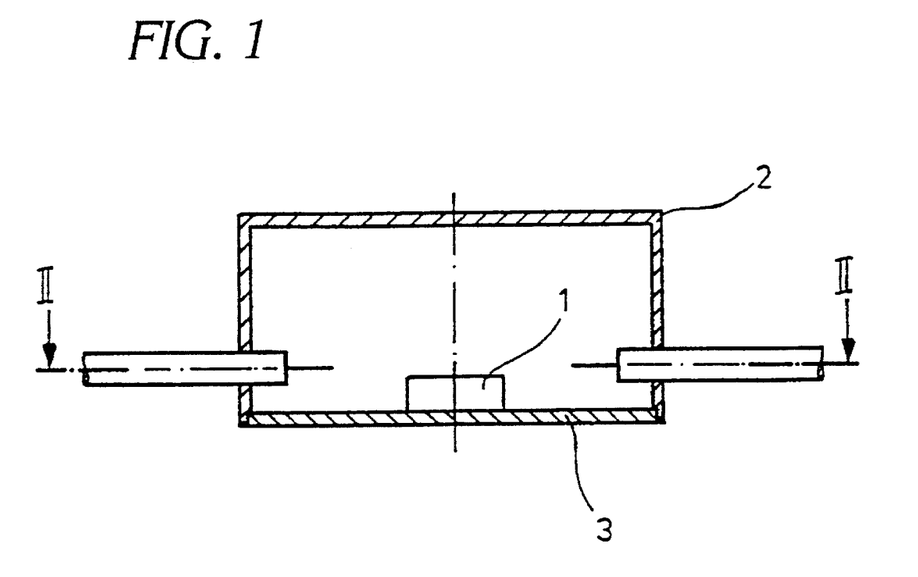
FIG. 1 shows a single rf resonator in an axial cross section having a dielectric resonator inside a case.
Figure 2:
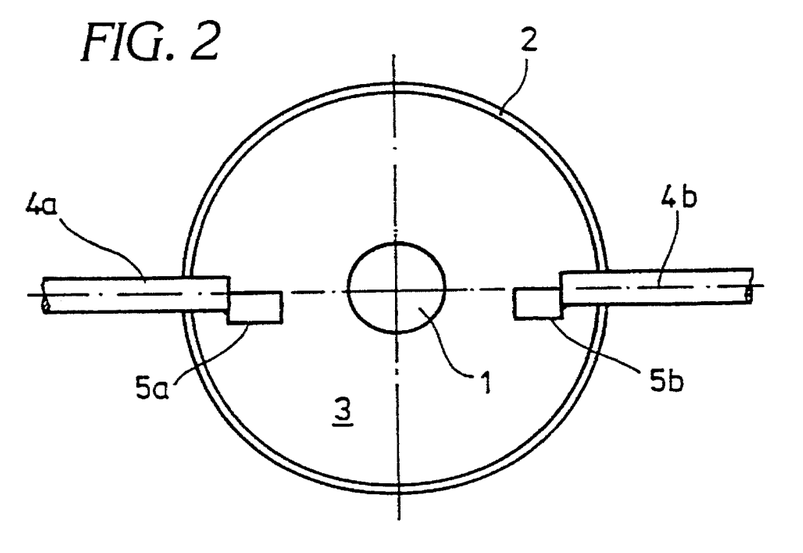
FIG. 2 shows a section taken along the line II—II from FIG. 1.

FIG. 1 shows a single rf resonator for the apparatus according to the present invention. The rf resonator has a cylindrical housing with a first section 2 of copper and a second section 3, which is one of the flat cylinder surfaces and which is permeable for electromagnetic waves and which may consist of e.g. ceramic or plastic material. Inside the case 2, 3 there is a disk shaped dielectric resonator 1, which in the example shown is directly attached to the base surface 3, which however as well may be held in another position by some means inside the housing. For coupling electromagnetic rf fields into the dielectric resonator 1 and for sensing of the resonator fields coaxial cables 4a and 4b resp. are provided on opposite sides of the case, ending in coupling loops 5a and 5b on their sides faced to the dielectric resonator 1, which form a simple conductor loop between the central conductor and the coaxial cable shield 4a and 4b, respectively. These conductor loops 5a and 5b serve as c transmitting and receiving means, respectively.

The following consideration may serve in the layout of a rotationally symmetrical solid state resonator, especially a disk shaped resonator with radius a and height h. For the z-component of the magnetic field inside the resonator the form $$H_z \propto J_0(k_d r)$$

and outside $$H_z \propto K_0(hr)$$

may be assumed, where $k_d$ and ih are the cutoff wave numbers inside and outside the resonator and $J_0$ and $K_0$ are the 0-order Bessel's functions for real and imaginary arguments. The cutoff wave numbers are related to the resonator wave number $\beta$ and to the wave number k for vacuum by the relation:

$$\beta_c^2 = k^2 - \beta^2$$

In the r- and z-direction the following boundary conditions have to be approximately fulfilled:

$$\beta_d^2 = \left(\frac{p_{01}}{a}\right)^2, \quad \beta^2 = \left(\frac{\pi}{L}\right)^2$$

where $P_{01}$, is the first root of $J_0$. Further:

$$k^2 = \omega^2/c^2 = \omega^2 \mu_r \mu_0 \epsilon_r \epsilon_0 = \kappa k_0^2, \quad \kappa = \epsilon_r \mu_r$$

Now assuming L=a, a frequency of 2.5 GHz, a typical value of $\epsilon_r$=38 for the resonator and $P_{01}$=2.405, we obtain from $$k^2 = \frac{\pi^2}{a^2} + \frac{p_{01}^2}{a^2} = \frac{(2\pi f)^2}{c^2} \epsilon_r$$

a resonator layout described by a=L=12.25 mm.

Furthermore tuning means are provided in the rf resonators to adjust the resonance frequency (not shown); they may e.g. consist of tuning bodies with an adjustable position with respect to the dielectric resonator. In the simplest case this may be a metallic screw, which may be turned into the metallic case 2, 3 to a certain depth thus arriving at a certain distance from the dielectric resonator. However, generally also dielectric or magnetic tuning bodies may be applied, the position of which may be adjusted manually or by a drive mechanism, which is controlled from external signals from the control and analysis unit. Alternatively tuning bodies of fixed position may be used, the dielectric, magnetic or metallic properties of which may be changed by electrical control signals, this again allowing an adjustment of the resonance frequency of the rf resonator.

The coupling loops 5a and 5b for input and output into and from the dielectric resonator 1 are of symmetrical construction, so that they may arbitraily be selected as transmitter or receiver loop. With the loop 5b considered as the receiver loop the signals induced into it by the field of the solid state resonator 1 are led to a measuring circuit, which generates a signal proportional to the amplitude of the resonator field by e.g. peak value rectification. After anlogue to digital conversion this signal will successively undergo further analysis in the control and analysis unit, which typically will comprise a microprocessor.

Figure 3A:
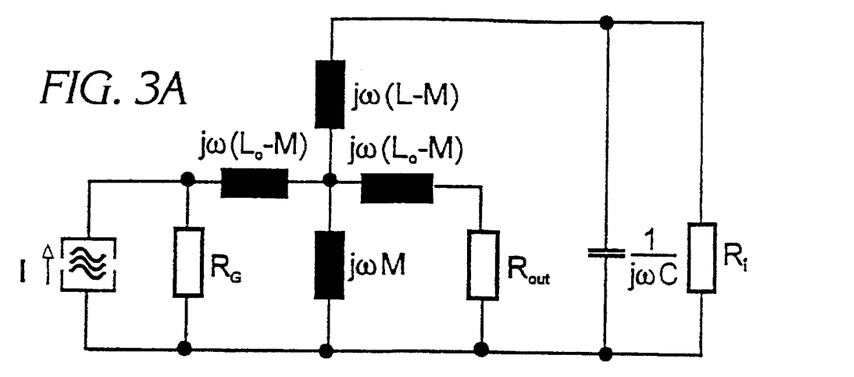
FIGS. 3A–C show diagrams of equivalent circuits to the resonator circuit.
Figure 4:
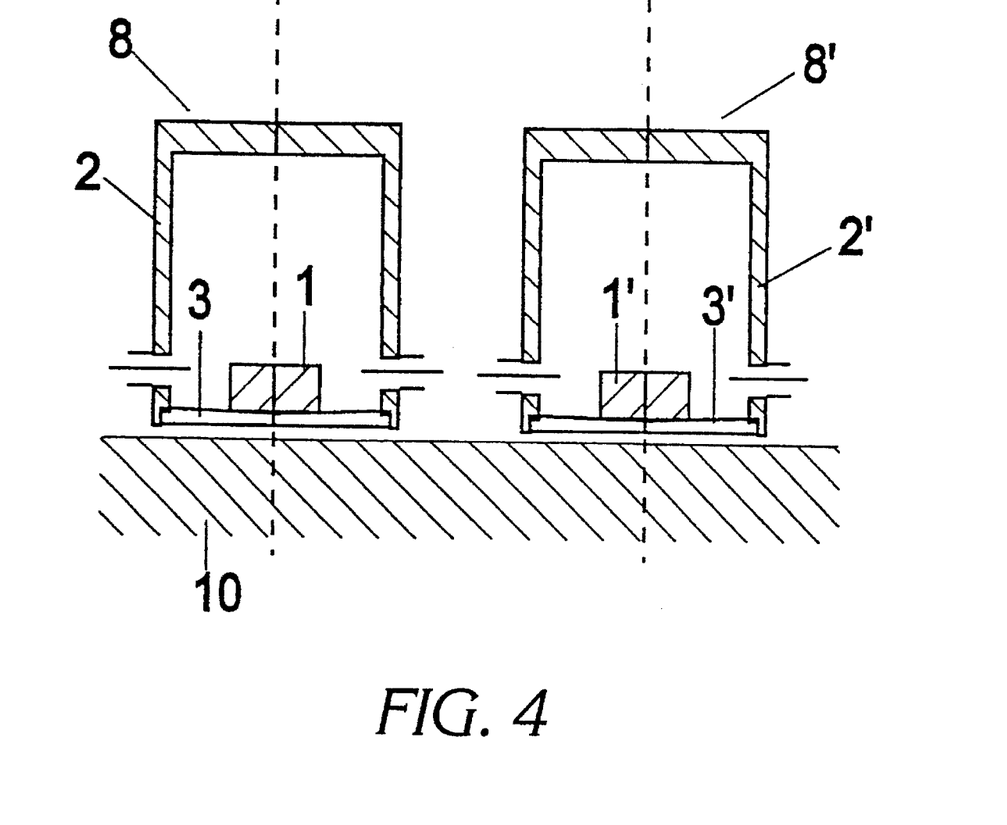
FIG. 4 shows a schematic view of two symmetrical resonators placed above the sample matter.

The following description will serve to explain the unique relationships between the dielectric properties of a material placed close to a resonator group of 2 symmetrical resonators as shown in FIG. 4 and the sum and difference of the signals from this group. For this purpose the equivalent circuit of a single rf resonator will be ragarded. In FIG. 3A an equivalent circuit for the rf resonator is shown as an RLC circuit. The rf field coupling by loops may be represented by a transformer circuit. Since the input and output coupling loops are placed on diametrically opposite positions of the solid state resonator, they may be regarded as parallel transformers. Combining both of these to the mutual inductance M the equivalent circuit from FIG. 3A results. Furthermore the following definitions of impedances shown at the circuit symbols will be used:

$R_G$ Source resistance of rf generator (constant current source)

$L_0$ Coupling loop inductance

L Resonator inductance

M mutual coupling inductance

C resonator capacitance $R_1$, resonator inner resistance $R_{out}$ output resistance Since the coupling loop 5a is completely contained inside the stray field of the dielectric resonator 1 we may with the number of windings equal to 1 assume that $$M = L_0$$

Furthermore it may be assumed:

$$R_{out} \gg \omega M$$

$$R_G \gg \omega M$$

Figure 3B:
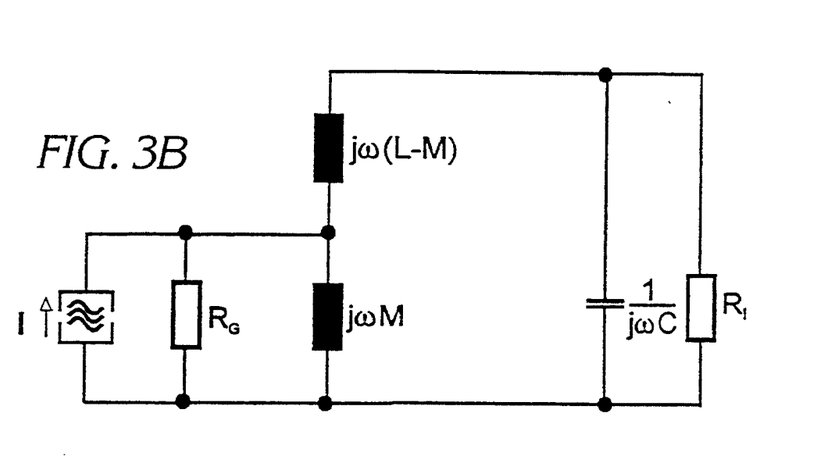

With these assumptions the equivalent circuit from FIG. 3A simplifies to the one shown in FIG. 3B.

In a next step the parallel impedance on the right hand side of FIG. 3B will under the assumption:

$$\omega \cdot C \cdot R_i = Q_i \gg 1$$

be transformed into the equivalent series impedance $$Z_s \approx \frac{1}{\omega^2 C^2 R_i} - j\frac{1}{\omega C}$$

Figure 3C:
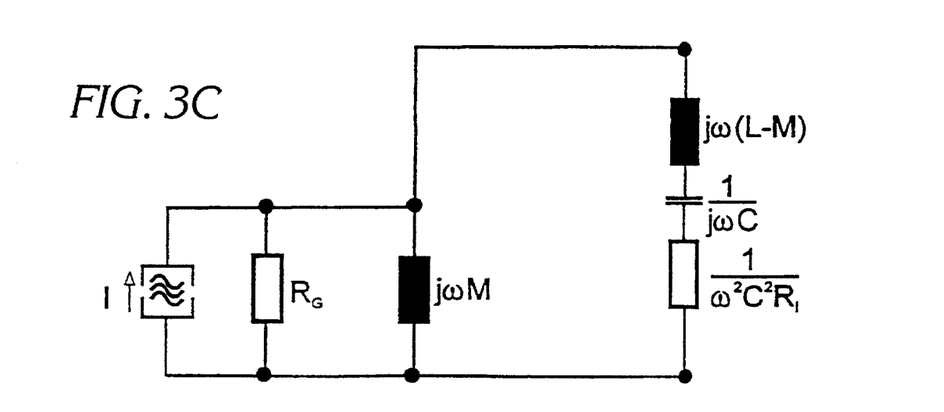

Then the equivalent circuit shown in FIG. 3C results. The input impedance of this circuit turns out to be:

$$Z_{in} = j\omega M + \frac{\omega^2 M \left[\frac{1}{\omega^2 C^2 R_i} - j\left(\omega L - \frac{1}{\omega C}\right)\right]}{\left(\frac{1}{\omega^2 C^2 R_i}\right)^2 + \left(\omega L - \frac{1}{\omega C}\right)^2}$$

Close to resonance the first expression may be neglected compared to the second leading to the following absolute value of the input impedance:

$$|Z_{in}| = \frac{\omega^4 M^2 C^2 R_i}{\sqrt{1 + \left(\omega L - \frac{1}{\omega C}\right)^2 (\omega^2 C^2 R_i)^2}}$$

Here it has ben used that $$\omega^2 C^2 R_i = \frac{\frac{\omega C}{G_i}}{\frac{1}{\omega C}} = \frac{Q_i}{\frac{1}{\omega C}} > 1$$

On the one hand this is due to the high $Q_1$-value of the unloaded dielectric resonator; on the other hand, close to the resonance frequency the value of $1/C$ is close to the value of L. The latter quantity may be easily determined since the inductance of a disk shaped dielectric resonator with the radius a and the height h is approximately given by $$L = \mu_0 a \left( \ln\frac{a}{h} + \frac{3}{2} \right)$$

which for typical values, a=6 mm, h=4 mm and a frequency of 2.5 GHz results in:

$$\omega L \approx 225 \, \Omega$$

Expanding the above expression for the input impedance $|Z_{in}|$ into a Taylor's series around the resonance frequency $\omega_0$ gives $$|Z_{in}| = \omega^4 M^2 C^2 R_i \left[ 1 - 2Q_i^2 \left( \frac{\Delta\omega}{\omega_0} \right)^2 \right]$$

where $$Q_i = \omega_0 C R_i$$

has been used.

Furthermore the coupling coefficient k will be introduced defined by $$k = M/L \approx L_0/L$$

where the above approximation $M \approx L_0$ has been used. The inductance $L_0$ of the coupling loop with the loop radius b and the conductor radius r is given by $$L_0 = \mu_0 b \left( \ln\frac{b}{r} + \frac{1}{4} \right)$$

At a frequency of 2.5 GHz, b=1.5 mm, r=0.5 mm $L_0$ =39 results. Then the coupling coefficient is k≅0.177.

The definition for k inserted into the formula for $|Z_{in}|$ leads to $$|Z_{in}| = k^2 \frac{\omega_0^4}{\omega^4} R_i \left[ 1 - 2Q_i^2 \left( \frac{\Delta\omega}{\omega_0} \right)^2 \right]$$

Finally the output resistance $R_{out}$ will be taken into account a posteriori. Since $R_1$ has a high value given by $$R_i = Q_i \frac{1}{\omega_0 C} \cong 2000 \cdot 225\Omega = 450 k\Omega$$

the whole factor in front of the brackets in the above equation for $|Z_{in}|$ will become equal to the output resistance if this is assumed to be sufficiently small. This finally gives:

$$|Z_{in}| = R_{out} \left[ 1 - 2Q_i^2 \left( \frac{\Delta\omega}{\omega_0} \right)^2 \right]$$

From this relation the influence of the material under investigation close to a solid state resonator may be deduced. The influence of small changes in $\epsilon'$ on $|Z_{in}|$ close to the resonance frequency $\omega_0$, i.e. $\Delta\omega = \omega - \omega_0 \ll \omega_0'$, as this will be caused by the presence of the material under investigation close to the resonator, may be described by:

$$\frac{d|Z_{in}|}{d\epsilon'} = \frac{d|Z_{in}|}{d\omega_0} \frac{d\omega_0}{d\epsilon'} = -2R_{out}Q_i^2 \frac{d}{d\omega_0} \left( \frac{\omega - \omega_0}{\omega_0} \right)^2 \frac{d\omega_0}{d\epsilon'}$$
$$= 4R_{out}Q_i^2 \frac{\omega(\omega - \omega_0)}{\omega_0^3} \frac{d\omega_0}{d\epsilon'}$$

Taking into account the relations $$\omega_0 = \frac{1}{\sqrt{LC}} = \frac{1}{\sqrt{LC_0\epsilon'}}$$

$$\frac{d\omega_0}{d\epsilon'} = -\frac{1}{2} \omega_0 \frac{1}{\epsilon'}$$

finally one obtains $$\Delta|Z_{in}| = -2R_{out}Q_i^2 \frac{\omega - \omega_0}{\omega_0} \frac{1}{\epsilon'} \Delta\epsilon' \propto \Delta\epsilon'$$

Here it has to be noted that the sign of change of $|Z_{in}|$ for increasing $\epsilon'$ depends on whether the resonance frequency $\omega_0$ is above or below the operating frequency $\omega$. I.e. in the case of two resonators operated symmetrically above and below the operating frequency the difference F1–F2 of the resonator signals is proportional to $\Delta\epsilon'$.

Now the influence of changes in the imaginary part of the dielectric constant will be considered. The imaginary part $\epsilon''$ is is contained already in the above equation $$|Z_{in}| = R_{out} \left[ 1 - 2Q_i^2 \left( \frac{\Delta\omega}{\omega_0} \right)^2 \right]$$

hidden in $Q_i$, which may be written as $$Q_i = \frac{1}{\tan(\delta)} = \frac{\epsilon'}{\epsilon''}$$

from which follows $$|Z_{in}| = R_{out} \left[ 1 - 2\frac{\epsilon'^2}{\epsilon''^2} \left( \frac{\Delta\omega}{\omega_0} \right)^2 \right]$$

From this the change in $|Z_{in}|$ with $\epsilon''$ results in:

$$\Delta|Z_{in}| = \frac{d|Z_{in}|}{d\epsilon''} \Delta\epsilon'' = -4R_{out} \frac{\epsilon'^2}{\epsilon''^3} \left( \frac{\Delta\omega}{\omega_0} \right)^2 \Delta\epsilon'' \propto \Delta\epsilon''$$

Here it has to be noted that, in contrast to the above dependence of $|Z_{in}|$ on $\epsilon'$, here the sign of $|Z_{in}|$ with changing $\epsilon''$ does not depend on whether the resonator will be operated above or below the resonance frequency $\omega_0$. Then it may be deduced that in the case of two resonators tuned symmetrically above and below the operating frequency the sum of the resonator signals is proportional to $\Delta\epsilon''$. As may be seen above, due to the sign reversal the effects of changes in $\epsilon'$ compensate for each other in the sum, so that the sum is sensitive to changes in $\epsilon''$ only.

The difference, which is proportional to $\Delta\epsilon'$ as seen above is in turn not influenced by changes in $\epsilon''$ since they occur with the same signs for the first and for the second resonator and consequently compensate for each other in the difference.

Summarizing it follows that with a symmetrical pair of resonators the sum and the difference of the measured signals F1 and F2 are 'orthogonal' to each other, so that the effects due to $\epsilon'$ and $\epsilon''$ will be decoupled. The sums and differences may be normalized by $$\Delta\epsilon' \propto \frac{F1-F2}{F1_0+F2_0}$$

$$\Delta\epsilon'' \propto \frac{F1_0+F2_0-(F1+F2)}{F1_0+F2_0}$$

where F10 and F20 are the resonator signals of the first and second resonator under no load conditions, i.e. in absence of the matter under investigation.

FIG. 4 shows two rf resonators adjacent to each other, with their field permeable sections 3 faced towards the matter 10 to be measured, whereas their conductive case sections shield against mutual interaction of the resonator fields. By the metallic case sections 2 the hemisphere above the resonators 1 is shielded; furthermore a certain directivity will be achieved by virtue of which the resonator field from the dielectric resonator 1 will be directed towards the matter under investigation.

Figure 5:
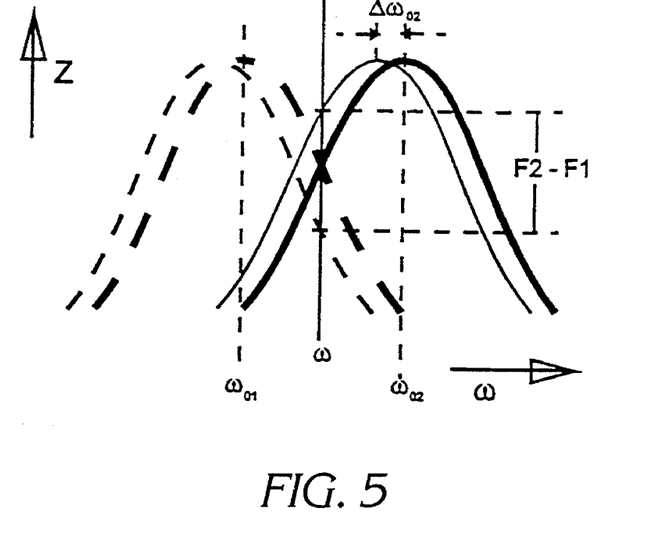
FIG. 5 shows resonance curves of the first (dashed) and of the second resonator (full line) without sample matter (fat) and with sample matter (thin lines), wherein $\Delta\epsilon''=0$.

The rf resonators 8, 8' are supplied with the same rf field of frequency ω via the coupling loops (4a in FIG. 1). Both the rf resonators 8, 8' have been pre-adjusted in such a way that under no load conditions (in the absence of the matter to be measured) they have the different resonance frequencies $\omega_{01}$ and $\omega_{02}$. This preadjustment is performed by the tuning means mentioned above. The constant operating frequency ω is adjusted as to be centered between the resonance frequencies $\omega_{01}$ and $\omega_{02}$. These relationships are shown in FIG. 5, wherein the fat dashed (full line) curve shows the resonance curve of the first (second) resonator in the absence of matter in front of the resonators. The operating frequency is located exactly in the centre between the resonance frequencies $\omega_{01}$ and $\omega_{02}$.

With the matter under investigation brought close to the resonators as shown in FIG. 4, the situation described by the thin lines develops. For the purpose of a simple graphical description it has been assumed here that a change in the real part only of the dielectric constant takes place, i.e. $\Delta\epsilon''=0$. In this case the inluence of the matter brought close to the resonator group leads to a displacement of both the resonance curves from the symmetrical position with respect to the operating frequency ω. In consequence both the resonators are no longer operated in symmetrical operating points with respect to the fixed operating frequency ω, i.e. in the same distance from their resonance frequencies, but rather the operating point moves uphill on the one resonance curve towards the resonance frequency ($\omega_{02}$) and downhill on the other resonance curve off the resonance frequency ($\omega_{01}$). This behaviour corresponds to the result found above, that with changing $\epsilon''$ the changes of Δ|Zin| occur in opposite directions for resonance frequencies located below and above the operating frequency. The rf resonators originally working symmetrically around the operating frequency now provide different output signals F1 and F2 (e.g. as measurement values the amplitude of the resonator field induced into the receiver loop 5b will be measured). This difference due to the presence of a material in front of the group of resoantors is indicated as F2–F1 in FIG. 5.

Figure 6:
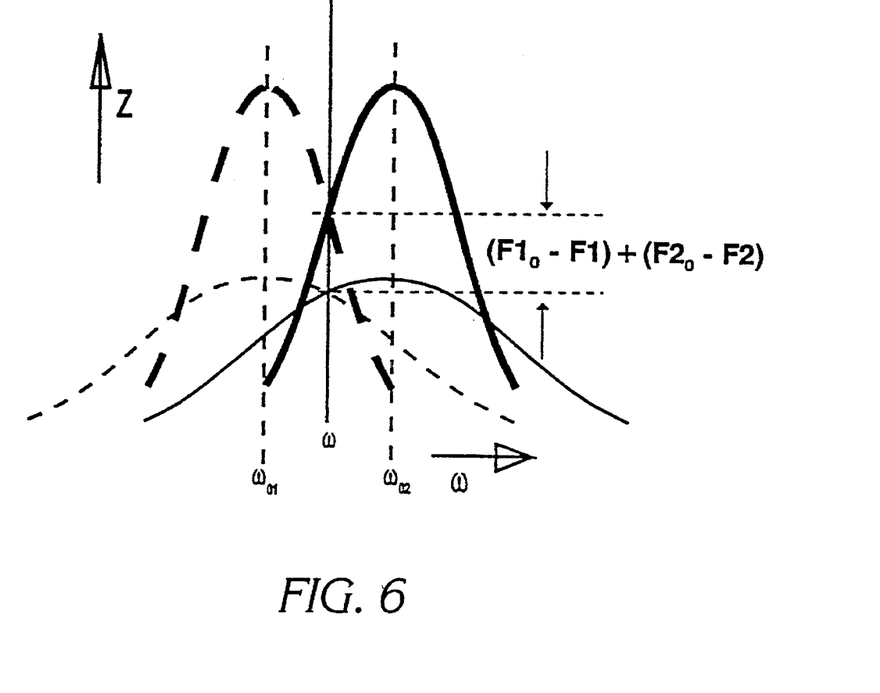
FIG. 6 shows resonance curves of the first (dashed) and of the second resonator (full line) without sample matter (fat) and with sample matter (thin lines), wherein $\Delta\epsilon'=0$.

In FIG. 6 in contrast the case will be considered that the presence of some material will cause a change of the imaginary part of the dielectric constant only, i.e. $\Delta\epsilon'=0$. In this case the resonance curves in turn experience no displacement but rather a broadening occurs, which is shown in thin lines. Therefore the difference of signals between both the resonators vanishes since the resonators are still operated symmetrically around the operating frequency ω. This behaviour corresponds to the result found above, that with changing $\epsilon''$ the changes of |Zin| occur in the same direction for resonance frequencies located below and above the operating frequency. However, a difference results between the sum F10+F20 in the absence of the material under investigation and the sum F1+F2 in its presence. The difference of these sums F10+F20–(F1+F2) is proportional to the change in $\epsilon''$ caused by the presence of the matter to be investigated.

The relations given above $$\Delta\epsilon' \propto \frac{F1-F2}{F1_0+F2_0}$$

$$\Delta\epsilon'' \propto \frac{F1_0+F2_0-(F1+F2)}{F1_0+F2_0}$$

are valid close to the resonance frequency only. However they describe the right qualitative signal behaviour even in greater distance from the resonance frequency. In those cases that the above analytical relations for $\epsilon'$ and $\epsilon''$ are no longer valid they may be replaced by refined calibration curves, which have been obtained empirically and are accessible in the control and analysis unit where they have been stored.

An especially useful further embodiment of the invention provides an additional pair of sensors besides the one shown in FIG. 4 which is again supplied with the same operating frequency ω and tuned to resonance frequencies symmetrically around this oparating frequency. Whereas the first pair of sensors is directed towards the matter under investigation as shown in FIG. 4, the second pair is directed towards a reference medium. The signals of the second pair of sensors undergo the same analysis scheme as the signals of the first pair. By comparison between the first pair of sensors directed towards the matter to be measured and the second pair of sensors directed towards the reference medium useful reference values result which may be used to calibrate the apparatus. E.g. the following may serve as reference media:

Empty space (air),

A reference medium with known properties, a dry sample of the same material as the one to be measured if the humidity of the latter is to be determined, a dielectric layer of known thickness, if the layer thickness of a layer from the same material is to be measured, a known distance to a dielectric body, if an unknown distance is to be measured.

I claim:

1. An apparatus for the measurement of the complex dielectric constant of a material by analysis of the amount of detuning of an rf resonator introduced by the presence of the material, the apparatus comprising rf transmitting means to transmit electromagnetic fields of variable high frequency to a rf resonator, receiving means for the resonator field and measurement means connected thereto, which allow determination of the amplitude of the received rf signals, characterised in that two rf resonators of identical construction (8,8') are provided, each of which comprises a dielectric solid state resonator (1,1') in a case having a first section (2,2'), which surrounds the solid state resonator with conductive material in at least one hemisphere, and a second section (3,3'), which is permeable for electromagnetic alternating fields, and means for adjusting the resonance frequency of the rf resonator, said two rf resonators are adapted to be arranged with respect to each other in such a way that their conductive case sections (2,2') shield them against mutual interference and that their sections permeable for electromagnetic fields (3,3') are directed towards the material (10) to be measured, and control and analysis means are provided which are adapted to control the rf transmission means and/or the rf resonators in such a way, that both rf resonators are supplied with rf fields of the same frequency ($\omega$) which, in the absence of the material to be measured, is centered between the differently pre-adjusted resonance frequencies ($\omega_{01}$, $\omega_{02}$) of the first and the second rf resonator (8, 8'), and to receive the measured amplitude values of each of the received rf signals and to determine, on the basis of their sum and difference values determines of said measured amplitude values, the complex dielectric constant.

2. Apparatus according to claim 1, characterised in that the second section (3) of the case consists of a dielectric material.

3. Apparatus according to claim 1, characterised in that the second case section of dielectric material consists of plastic or ceramic material.

4. Apparatus according to claim 1, characterised in that the first case section (2,2') of each rf resonator (8, 8') consists of a metallic cylinder with one of its flat base areas being completely or partly open, and the second section (3, 3') is formed by a dielectric wall, which lies in the openening of the base area.

5. Apparatus according to claim 1, characterised in that the second case section is at least partially open to allow measurement of gases and fluids.

6. Apparatus according to claim 1, characterised in that the first case section (2, 2') of each rf resonator (8, 8') consists of a metallic cylinder with one of its flat base areas being completely or partly open, wherein the diameter of the cylindrical section is smaller than half the cutoff wavelength of the case.

7. Apparatus according to claim 1, characterised in that the tuning means for the rf resonator comprise a dielectric, magnetic or metallic tuning body inside the case, the position of which with respect to the solid state resonator may be changed manually or controlled by the control and analysis means.

8. Apparatus according to claim 1, characterised in that the tuning means for the rf resonator comprise a dielectric, magnetic or metallic tuning body inside the case, the dielectric, magnetic or metallic properties of which may be changed by control signals from the control and analysis means.

9. Apparatus according to claim 1, characterised in that both of the rf resonators (8, 8') are positioned at an equal level above the material to be measured and adjacent to each other, so that their second case sections (3, 3') are directed towards the material to be measured.

10. Apparatus according to claim 1, characterised in that each of the dielectric resonators (1, 1') is made of a metal-oxide ceramic material.

11. Apparatus according to claim 1, characterised in that besides said two resonators (8, 8') a second pair of rf resonators of identical construction is provided which are coupled to the rf transmission means and to the control and analysis means in the same way as said two resonators (8, 8') and which are, independent of said two rf resonators, directable towards a reference medium.

12. A method for the measurement of the complex dielectric constant of a material by analysing the amount of detuning of an rf resonator introduced by the presence of the material, wherein high frequency electromagnetic fields of selectable frequency are coupled into the rf resonator, the resonator field is sensed via a receiving means and the amplitude of the received rf signals is determined by a measuring means, characterised by using two rf resonators (8, 8') each comprising a dielectric resonator (1, 1') in a case having a first section (2, 2'), which surrounds the solid state resonator at least in one hemisphere with conductive material, and a second section (3, 3'), which is permeable for electromagnetic alternating fields, and directing said two rf resonators towards the material to be measured in such a way, that their second case sections (3, 3') are facing the material (10) and that their first case sections (2, 2') shield against mutual interference due to electromagnetic fields emanating from the second case sections, tuning the first and the second rf resonator by a tuning means in such a way that, in the absence of the material under investigation, the first and the second resonator have a first ($\omega_{01}$) and a second ($\omega_{02}$) resonance frequency, respectively, with the second frequency being different from the first, and supplying both rf resonators with an electromagnetic field of a frequency ($\omega$), which is centered between the first ($\omega_{01}$) and the second ($\omega_{02}$) resonance frequency, and supplying the measured amplitude values of the received rf signals in said two resonators to a control and analysis means and determining the dielectric constant of the material under investigation in the control and analysis means on the basis of the sum and difference values of the measured amplitude values using predetermined relationships.

13. Method according to claim 12, characterised by using a predetermined relationship of the form $$\Delta\epsilon' \propto \frac{F1 - F2}{F1_0 + F2_0}$$

$$\Delta\epsilon'' \propto \frac{F1_0 + F2_0 - (F1 + F2)}{F1_0 + F2_0}$$

where F1 and F2 are the amplitude values of the received rf signals of the first and of the second rf resonator respectively, when they are directed towards the material to be measured, whereas F10 and F20 are the corresponding amplitudes in the absence of the material to be measured.

14. Method according to claim 12, characterised by using for the predetermined relationship a calibration curve, which has been predetermined experimentally.

15. Method according to claim 12, characterised by providing a second pair of rf resonators of identical construction as said two resonators (8, 8'), which are supplied with the same operating frequency ($\omega$) and the sensed rf signals of which are analysed in the control and analysis means in the same way as those of said two resonators (8, 8'), and by directing said second pair of resonators towards a reference medium and using the values of the second pair as reference quantities.

16. Method according to claim 12, characterised by providing a second pair of rf resonators of identical construction as said two resonators (8, 8'), which are supplied with the same operating frequency ($\omega$) and the sensed rf signals of which are analysed in the control and analysis means in the same way as those of said two resonators (8, 8'), by directing the second rf resonator pair towards empty space, and by using the values of the second pair as reference quantities.

17. Method according to claim 12, characterised by providing a second pair of rf resonators of identical construction as said two resonators (8, 8'), which are supplied with the same operating frequency (ω) and the sensed rf signals of which are analysed in the control and analysis means in the same way as those of said two resonators (8, 8'), by directing the second rf resonator pair towards a dry sample of the medium to be measured, and by using the values of the second pair as reference quantities.

18. Method according to claim 12, characterised by providing a second pair of rf resonators of identical construction as said two resonators (8, 8'), which are supplied with the same operating frequency (ω) and the sensed rf signals of which are analysed in the control and analysis means in the same way as those of said two resonators (8, 8'), by directing the second rf resonator pair towards a sample of the medium to be measured having a known humidity, and by using the values of the second pair as reference quantities.

19. Method according to claim 15, characterised by providing a second pair of rf resonators of identical construction as said two resonators (8, 8'), which are supplied with the same operating frequency (ω) and the sensed rf signals of which are analysed in the control and analysis means in the same way as those of said two resonators (8, 8'), by directing the second rf resonator pair towards a dielectric layer of the material to be measured with known thickness, and by using the values of the second pair as reference quantities.

* * * * *